US009023331B2

(12) United States Patent
Jones et al.

(10) Patent No.: US 9,023,331 B2
(45) Date of Patent: May 5, 2015

(54) USE OF A CATIONICALLY MODIFIED HYDROLYSED STARCH AS A HAIR FIXATIVE

(75) Inventors: Roger Trevor Jones, Cheshire (GB); Debra Louise Jones, North Yorkshire (GB)

(73) Assignee: Croda International PLC, Goole, North Humberside (GB)

( * ) Notice: Subject to any disclaimer, the term of this patent is extended or adjusted under 35 U.S.C. 154(b) by 791 days.

(21) Appl. No.: 10/598,702

(22) PCT Filed: Mar. 9, 2005

(86) PCT No.: PCT/GB2005/000906
§ 371 (c)(1),
(2), (4) Date: May 3, 2007

(87) PCT Pub. No.: WO2005/084620
PCT Pub. Date: Sep. 15, 2005

(65) Prior Publication Data
US 2007/0292376 A1    Dec. 20, 2007

(30) Foreign Application Priority Data

Mar. 9, 2004  (GB) .................................. 0405236.1

(51) Int. Cl.
A61K 8/73      (2006.01)
A61Q 5/06      (2006.01)
C08B 31/00     (2006.01)
C08B 31/12     (2006.01)

(52) U.S. Cl.
CPC . *A61Q 5/06* (2013.01); *A61K 8/732* (2013.01); *A61K 2800/5426* (2013.01); *C08B 31/12* (2013.01)

(58) Field of Classification Search
None
See application file for complete search history.

(56) References Cited

U.S. PATENT DOCUMENTS

| 2,813,093 A | 11/1957 | Caldwell et al. |
| 3,186,911 A | 6/1965 | Rieger et al. |
| 3,639,389 A | 2/1972 | Hull |
| 6,096,524 A * | 8/2000 | Shi et al. .......................... 435/99 |
| 2001/0007655 A1 | 7/2001 | Paul et al. |
| 2001/0018046 A1 * | 8/2001 | Vitale et al. ................. 424/70.16 |
| 2003/0129210 A1 | 7/2003 | Chowdhary |
| 2006/0002880 A1 * | 1/2006 | Peffly et al. ................. 424/70.13 |

FOREIGN PATENT DOCUMENTS

| EP | 0577519 | * | 1/1994 |
| EP | 0577519 A1 | | 1/1994 |
| EP | 0 948 959 A2 | | 10/1999 |
| EP | 0948958 | | 10/1999 |
| EP | 1 162 208 A1 | | 12/2001 |
| GB | 1 285 547 A | | 8/1972 |
| JP | 54-86629 A | | 7/1979 |
| JP | H11-335247 | | 12/1999 |
| WO | 01/39721 A2 | | 7/2001 |
| WO | 01/80902 A2 | | 11/2001 |
| WO | 01/96403 A1 | | 12/2001 |

OTHER PUBLICATIONS

European Patent Office, International Search Report and Written Opinion of the International Searching Authority, Mailed Jun. 15, 2005 (9 pages).
UK Intellectual Property Office, Patents Act 1977 Search Report Under Section 17, Application No. GB0504863.2, May 23, 2005 (1 page).
UK Intellectual Property Office, Patents Act 1977 Examination Report Under Section 18(3), Application No. GB0504863.2, Jul. 14, 2006 (1 page).
"Starch." Wikipedia, The Free Encyclopedia. Wikimedia Foundation, Inc. last edited Jun. 11, 2011; downloaded from Web Jun. 15, 2011.
Examination Report mailed Nov. 25, 2010 in corresponding Japanese Application No. 2007-502394.

* cited by examiner

*Primary Examiner* — Scott Long
*Assistant Examiner* — Sarah Alawadi
(74) *Attorney, Agent, or Firm* — Jones Day

(57) ABSTRACT

The present invention relates to a hair fixative composition comprising a canonically modified hydrolysed starch and especially canonically modified hydrolysed starches, hydrolysed to the extend of having a dextrose equivalent of 1 to 6.

9 Claims, 4 Drawing Sheets

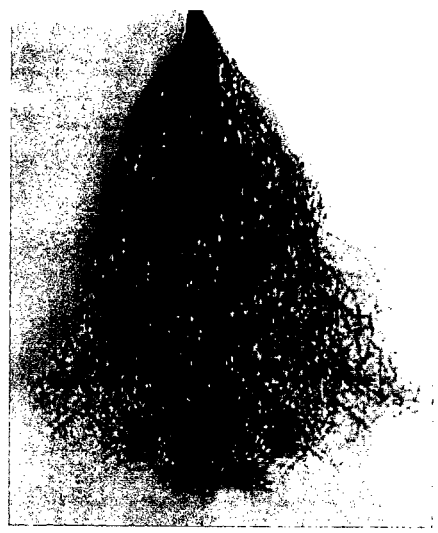
Fig.9
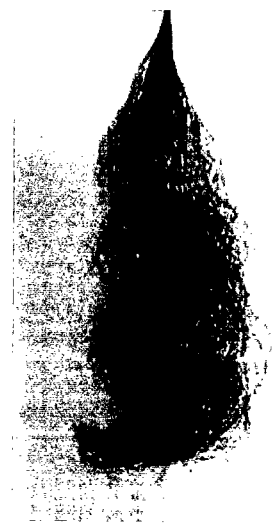 
Fig.10  Fig.11

USE OF A CATIONICALLY MODIFIED HYDROLYSED STARCH AS A HAIR FIXATIVE

The present invention relates to compositions useful in hair care or hair cosmetic formulations. It is particularly applicable to the preparation and use of cationically modified hydrolysed starch in hair fixative formulations. In particular, it relates to hair-setting compositions containing a film-forming cationically modified hydrolysed starch.

Hair fixative formulations are designed to provide a temporary setting effect or curl to the hair. These formulations contain a film-forming polymer in a delivery system which is usually a solvent or dispersant for the film-forming polymer. The hair setting or styling process usually involves the application of an aqueous solution or dispersion containing one or more film-forming materials to hair that is either wet, damp or dry. The treated hair can be wound on curlers or otherwise styled. The styling process involves application of the film-forming agent to deposit a coating on the hair which remains after drying. This film is required to be flexible and it mechanically hinders the hairs movement back to its natural shape. The dried film creates an overall stiffening of the hair and the fusing of strands together resulting in a greater resistance to deformation of the hairstyle. The hygroscopic properties of the film should be as low as possible to protect the hair from moisture uptake from the environment hence, hindering the disruption of the hydrogen bonds within the hair, leading to a loss of styling effect.

To be effective, the film-forming ingredients of a hair cosmetic composition preferably meet a number of requirements. The film derived from these ingredients should be flexible, yet possess strength and elasticity. The ingredients should display good adhesion to hair so as to avoid dusting or flaking off with the passage of time or when the hair is subjected to stress during normal grooming practices; should remain free of tack or gumminess under humid conditions; should be clear, transparent, glossy, and should maintain clarity upon aging. The ingredients should maintain good anti-static properties to prevent flyaway and should be easily removable by washing with a hair detergent.

UK patent 1,015,935 (U.S. Pat. No. 3,186,911) describes the use of tertiary amino alkyl esters of cornstarch with a low amylose content for use in a hair setting composition. This patent is concerned with unhydrolysed starch which has the disadvantage of the need to pre-heat the modified starch at 75-85° C. to produce a gelatinous dispersion with limited water solubility. In contrast, the present invention uses hydrolysed starch which removes the need for this pre-heat treatment. The hydrolysis also renders a product which forms a low viscosity/free-flowing solution that is easier to handle than the gelatinous non-hydrolysed starch. This patent also states that the composition of the starch with relation to amylopectin (50-75 parts) and amylose (25-50 parts) is important for optimum film-forming properties and adhesion properties. Our invention does away with this requirement.

UK patent 1,285,547 discloses the use of starch modified with tertiary amine reagents to produce quaternised starch. This patent describes the use of high amylose (more than 50% by weight) starch as the starting material before modification with tertiary amine quaternising agent. The cationic starch referred to in this patent also needs to be pre-heated to form a starch dispersion prior to use.

U.S. Pat. No. 3,186,911 (Warner Lambert) also describes starches modified with tertiary amine reagents. As with GB1, 285,547, this reference specifies that the amylose and amylopectin content of the final product must be in the range of 25 to 50 parts by weight and 75 to 50 parts by weight respectively.

US2003/0175230 (ClaudeDubief) describes starch betaine derivatives containing an ester linkage. Such compositions are not described as having hair fixative properties but rather are described as being used in shampoos and hair styling lotions.

JP54086629 describes a cosmetic base composed of a cationically-modified starch having a high quaternary nitrogen atom content. It is described as a base for shampoos or as a base for a skin care cosmetic. There is no indication that the compounds in question could have hair fixative properties.

U.S. Pat. No. 2,813,093 (National Starch Producers Inc), Wooo/15669 (Raisio Chemicals OY) and U.S. Pat. No. 3,854,970 (Nalco Chemical Company) describe various cationically modified starches for use in the paper industry. There is no indication that these compounds could possess hair fixative properties or have beneficial use in any other context than in paper production.

U.S. Pat. No. 6,344,183 concerns the use of non-ionically modified starch or optionally non-ionically modified hydrolysed starch. These compounds can be further modified with anionic or cationic compounds. The purpose of the non-ionic modification is to render the starch derivative water soluble and so more efficacious from water based formulations.

Whilst some of the above prior art references make reference to the use of hydrolysed starches as starting materials, none make any reference to the Dextrose Equivalent of the hydrolysed starch product which was used. Nor is there any indication that the Dextrose Equivalent is a relevant factor in any of the properties of subsequent product.

Surprisingly, and contrary to the teaching of the prior art, the present invention demonstrates that a hydrolysed starch with a Dextrose Equivalent of ≥1 and up to 6 which has been modified to contain cationic groups, is more efficacious as a fixative agent from water based styling compositions than commonly used film-forming polymers.

SUMMARY OF THE INVENTION

According to a first aspect of the present invention there is provided a hair fixative composition comprising a cationically modified hydrolysed starch wherein the hydrolysed starch is hydrolysed to the extent of having a dextrose equivalent ≥1 and up to 6.

Preferably the hair fixative composition contains from 0.5 to 25% by weight of cationically modified hydrolysed starch.

In a preferred embodiment the hair fixative composition contains 1% to 10% by weight of cationically modified hydrolysed starch.

In a preferred embodiment the hydrolysed starch is hydrolysed to the extent of having a dextrose equivalent of ≥1 to about 4.

In a particularly preferred embodiment the hydrolysed starch is hydrolysed to the extent of having a dextrose equivalent of about 2.

Preferably the hydrolysed starch is cationically modified using a reagent containing a group selected from amino, imino, ammonium, sulfonium, or phosphonium groups.

Preferably the hydrolysed starch is cationically modified using a reagent containing a tertiary amine or quaternary amine group and more preferably using a reagent selected from the group comprising 3-chloro-2-hydroxypropyltrimethylammonium chloride and epoxytrimethylammonium chloride.

According to a second aspect of the invention there is provided a method of use of a cationically modified hydrolysed starch as a hair fixative agent in a hair fixative composition, including the use of a cationically modified hydrolysed starch as defined above as a hair fixative agent in hair cosmetic formulations to improve the appearance and tactile properties of hair compared with market accepted styling fixatives.

According to a third aspect of the present invention there is provided a cationically modified hydrolysed starch suitable for use in a hair fixative composition.

In a particularly preferred embodiment the hydrolysed starch is hydrolysed to the extent of having a dextrose equivalent of about 2.

Preferably the hydrolysed starch is cationically modified using a reagent containing a group selected from amino, imino, ammonium, sulfonium, or phosphonium group.

In a preferred embodiment the hydrolysed starch is cationically modified using a reagent containing a tertiary amine or quaternary amine group and more preferably using a reagent selected from the group comprising 3-chloro-2-hydroxypropyltrimethylammonium chloride and epoxytrimethylammonium chloride.

BRIEF DESCRIPTION OF THE FIGURES

FIG. 9: Evaluation of frizz reductions of treated hair.
FIG. 10: Evaluation of frizz reductions of treated hair.
FIG. 11: Evaluation of frizz reductions of treated hair.

DESCRIPTION OF THE PREFERRED EMBODIMENTS

Figure 1:
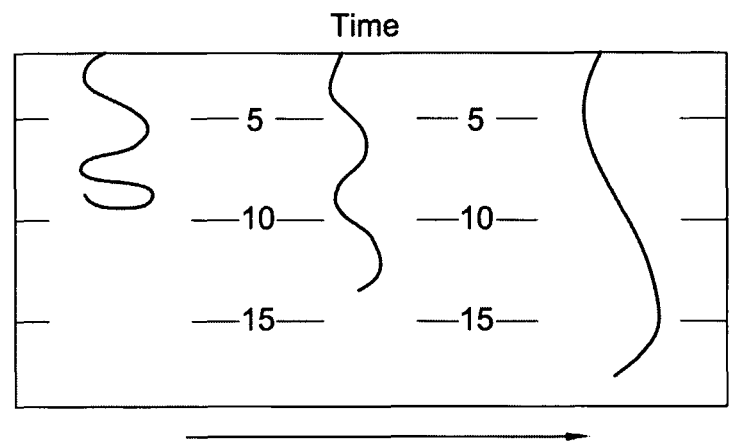
FIG. 1: Measurement of curl retention over time by suspending hair in front of a measuring panel.

The present invention is directed to hair cosmetic compositions, i.e., hair sprays, hair spritzes, hair gels, hair mousses, shampoos, conditioners and other hair cosmetic compositions.

The hair cosmetic composition preferably contains an effective amount of hydrolysed cationic starch according to the present invention, typically from about 0.5 to about 25%, but more typically from about 1 to about 10% by weight. Use of such starches is novel and advantageous in that they provide a clear solution with low viscosity and good spray characteristics. Furthermore, the resultant composition provides a clear film which is not tacky, has good hold and improved humidity resistance.

One advantage of the present invention is that all hydrolysed cationic starches are suitable for use herein. The starch used as the basis of the invention may be derived from any native source. A native starch is one as it is found in nature. Also suitable are starches derived from a plant obtained by standard breeding techniques including crossbreeding, translocation, inversion, transformation or any other method of gene or chromosome engineering. In addition, starch derived from a plant grown from artificial mutations and variations of the above generic composition which may be produced by known standard methods of mutation breeding are also suitable. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, and waxy or high amylose varieties thereof.

The starch hydrolysis may be accomplished by any method known in the art, such as by enzymes, acid, dextrinization, man-ox, or oxidation. The starch is hydrolysed to yield a dextrose equivalent of between $\geq 1$ and 6. A particularly preferred dextrose equivalent is about 2.

The enzymatic hydrolysis of the starch is carried out using techniques known in the art. Any enzyme or combination of enzymes, known to degrade starch may be used, particularly endo-enzymes. Enzymes useful in the present application include, but are not limited to, alpha-amylase, beta-amylase, maltogenase, glucoamylase, pullulanase, particularly alpha-amylase and pullalanase. The amount of enzyme used is dependent upon the enzyme source and activity, base material used, and the amount of hydrolysis desired. Typically, the enzyme is used in an amount of from about 0.01 to about 1.0%, particularly from about 0.01 to 0.3%, by weight of the starch.

The optimum parameters from enzyme activity will vary depending upon the enzyme used. The rate of enzyme degradation depends upon factors known in the art, including the enzyme concentration, substrate concentration, pH, temperature, the presence or absence of inhibitors, and the degree and type of modification. These parameters may be adjusted to optimise the digestion rate of the starch base.

It will be appreciated that such hydrolysis reactions do not necessarily lead to a product having a DE value which is a whole number. Any DE values should therefore be considered as being "approximately" or "about" the stated value and could be ±1 above or below the quoted value.

Cationic modification of the present invention can be from 0.1 g to 25 g of cationic agent per 100 g hydrolysed starch, more preferably 5 g to 20 g of cationic agent per 100 g hydrolysed starch. The cationic modification can be carried out before or after hydrolysis of the starch. Methods for the cationic modification of starches are known per se. Typically such methods, for example, involving reacting the starch through an etherification or esterification reaction with a reagent which will introduce into the starch a cationic group. The cationic modification may be accomplished by any reagent known in the art including those containing amino, imino, ammonium, sulfonium, or phosphonium groups. Such cationic derivatives include those with nitrogen containing groups comprising primary, secondary, tertiary and quaternary amines and sulfonium and phosphonium groups attached through either ether or ester linkages. A particularly preferred cationic modification involves quaternary ammonium etherification of starch, typically by treatment of starch with 3-chloro-2-hydroxypropyltrimethylammonium chloride ammonium chloride.

The above description of cationic modifications is not intended to be in any way limiting. It will be appreciated that the present invention is intended to encompass any method of introducing a cationic group into a starch, both those which are already known and those which are yet to be discovered.

The present invention is therefore directed to cationic hydrolysed starches, more particularly to trimonium hydroxypropyl hydrolysed starches.

Method for Producing Cationic Hydrolysed Starch

Preparation 1

Hydrolysed starch (e.g. Glucidex 2 supplied by Roquette UK Ltd) (100 g) and mains water (400 g) were weighed into a beaker and heated to 40° C. The pH of the reaction liquid was raised to 11.0-11.5 by adding 25% NaOH. 3-chloro-2-hydroxypropyltrimethylammonium chloride (Quab 151 ex. Degussa) (18.6 g) was added to the liquor dropwise via a separating funnel over a one hour period. The reaction liquid was then stirred at 40° C. for 16 hours.

Citric acid (1.0% w/w, 5.1 g) and trisodium citrate (0.5% w/w, 2.6 g) were added to the reaction liquid to buffer the pH. The pH of the reaction liquid was adjusted to 4.0-4.5 using either 25% NaOH or 28% HCl. The product was preserved using cosmetic grade chemical preservative. The product was filtered through a depth filter pad to produce a clear liquid.

Preparation 2

Hydrolysed starch (e.g. Glucidex 6 supplied by Roquette UK Ltd) (200 g) and mains water (800 g) were weighed into a beaker and heated to 40° C. The pH of the reaction liquid was raised to 11.0-11.5 by adding 25% NaOH. 3-chloro-2-hydroxypropyltrimethylammonium chloride (Quab 151 ex. Degussa) (37.2 g) was added to the liquor dropwise via a separating funnel over a one hour period. The reaction liquid was then stirred at 40° C. for 16 hours.

Citric acid (1.0% w/w, 10.0 g) and trisodium citrate (0.5% w/w, 5.0 g) were added to the reaction liquid to buffer the pH. The pH of the reaction liquid was adjusted to 4.0-4.5 using either 25% NaOH or 28% HCl. The product was preserved using cosmetic grade chemical preservative. The product was filtered through a depth filter pad to produce a clear liquid.

Preparation 3

Hydrolysed starch (e.g. Glucodry 310 supplied by Tate & Lyle UK Ltd) (200 g) and mains water (800 g) were weighed into a beaker and heated to 40° C. The pH of the reactor liquid was raised to 11.0-11.5 by adding 25% NaOH. 3-chloro-2-hydroxypropyltrimethylammonium chloride (Quab 151 ex. Degussa) (37.2 g) was added to the liquor dropwise via a separating funnel over a one hour period. The reaction liquid was then stirred at 40° C. for 16 hours.

Citric acid (1.0% w/w, 10.1 g) and trisodium citrate (0.5% w/w, 5.1 g) were added to the reaction liquid to buffer the pH. The pH of the reaction liquid was adjusted to 4.0-4.5 using either 25% NaOH or 28% HCl. The product was preserved using cosmetic grade chemical preservative. The product was filtered through a depth filter pad to produce a clear liquid.

TEST EXAMPLES

Example 1

Determination of Curl Retention at High Humidity of Hair Sprays

Curl Retention Protocol

Curl retention analysis had been concluded to be the most accurate method for assessing the holding properties of styling aids, especially for those that are intended for application onto wet or damp hair.

Calibrated hair samples are treated with the intended product and rolled onto curlers of a known size under specified conditions. The hair samples are left to set, after which they are suspended in front of a measuring panel (see FIG. 1), along with control hair samples that have been set with water. The length of the curl is then recorded and the samples are then allowed to relax under controlled temperature and humidity.

The length of the curl will increase over time; the rate and extent to which the swatch increases in length provides relevant information on the relative effectiveness of the fixative on style and hold.

Materials used in Example 1
Virgin European hair (de Meo)
10% Sodium laureth sulphate (SLES)
Spray formulation without active
Spray formulation with Preparation 1 (2.5% active).
Spray formulation with ISP Gafquat 755 N (polyquaternium-11) (2.5% active)
Spray formulation with ISP PVP K-90 (PVP) (2.5% active)
Spray formulation with ISP PVP/VA E-735 (PVP/VA Copolymer) (2.5% active)
Spray formulation with Preparation 2 (2.5% active)
Spray formulation with Preparation 3 (2.5% active)

| Aqueous hair spray formulation | |
|---|---|
| | % by Wt |
| Water | up to 100 |
| Ethanol DEB 100 | 30 |
| Natrasol (HEC) 2% solution | 5 |
| Active under test | qs (to provide 2.5% of active) |
| TEA | to pH 6.0 |

Study Procedure
1. Tresses of virgin European hair were cut into swatches of 15 mm in width and labelled A-F to provide six sets of samples.
2. All swatches were wetted by quick submersion in water then soaked in a 10% SLES solution for 30 seconds and finally rinsed in water.
3. The A swatch had excess water removed and the length recorded.
4. The B swatch was immersed in Preparation 1 test solution (2.5% active) for 2 minutes, excess solution was removed and length recorded.
5. The C swatch was immersed in the Gafquat 755N test solution (2.5% active) for 2 minutes, excess solution was removed and length recorded.
6. The D swatch was immersed in the PVP K-90 test solution (2.5% active) for 2 minutes, excess solution was removed and length recorded.
7. The E swatch was immersed in the PVP/VA E-735 test solution (2.5% active) for 2 minutes, excess solution was removed and length recorded.
8. The F swatch was immersed in the test formulation containing no active for 2 minutes, excess solution was removed and length recorded.
9. All swatches were then curled onto rollers and allowed to dry under ambient conditions for 1 hour before being conditioned at 50% (Relative humidity) RH and 20-25° C. overnight
10. All swatches were then removed from the rollers and curl length determined.
11. All swatches were then maintained at 80% RH and 20-25° C. Curl length was recorded at 15, 30, 60 and 120 minutes.
12. The procedure was repeated to yield a total of four paired evaluations.

A calculation was used to report the results in a format expressing the effect of the treatment on curl drop-out of the swatches as a function of time. The calculation, expressed as a percentage, is as follows:

$$\text{Percentage curl retention} = \frac{L - L_t}{L - L_o} \times 100$$

Where:

$L$=Length of tress prior to curling $L_t$=Length of curled tress at time t minutes $L_0$=Length of curled tress at zero minutes This was calculated for each tress before being averaged. The results are shown in table 1.

TABLE 1A

| | % retention at time (minutes) | | | | |
|---|---|---|---|---|---|
| | 0 | 15 | 30 | 60 | 120 |
| Preparation 1 | 100 | 96.12 | 93.04 | 87.59 | 79.77 |
| Gafquat 755N | 100 | 97.64 | 90.74 | 83.14 | 77.19 |
| PVP K-90 | 100 | 92.44 | 83.96 | 76.56 | 66.58 |
| PVPA/A 3-735 | 100 | 92.67 | 83.62 | 71.43 | 53.42 |
| Formulation | 100 | 93.64 | 78.42 | 66.71 | 51.51 |
| Water | 100 | 84.39 | 73.06 | 63.55 | 51.33 |

TABLE 1B

| | % retention at time (minutes) | | | | |
|---|---|---|---|---|---|
| | 0 | 15 | 30 | 60 | 120 |
| Preparation 2 | 100 | 66.67 | 58.33 | 52.78 | 50.00 |
| Preparation 3 | 100 | 60.53 | 52.63 | 26.32 | 23.68 |
| Water | 100 | 41.38 | 31.03 | 13.79 | 13.79 |

Preparation 2 is based on 6DE hydrolysed starch

Preparation 3 is based on 31DE hydrolysed starch

The study demonstrates that all of the test solutions did show an increase in curl retention above that of water alone. The formulation that included Preparation 1 consistently proved to be the most effective at curl retention, displaying 79.8% (p<0.001) curl retention after two hours at 80% RH and 20-25° C. The second most effective active within this test was shown to be Gafquat 755N, displaying 77.2% (p<0.001) curl retention after two hours at 80% RH 20-25° C.

Example 2

Sensory Evaluation of a Basic Hair Spray Formulation

The objective of the study was to evaluate the affect of the present invention on the tactile properties and appearance of hair, and compare it to a market accepted styling fixative (Gafquat 755N). Assessment was carried out using a panel of assessors.

Materials Used in Example 2

Virgin European hair (de Meo)

10% Sodium laureth sulphate (SLES)

Hair spray formulation

Hair spray formulation with Preparation 1 (2.5% active).

Hair spay formulation with Gafquat 755N (polyquaternium-11) (2.5% active)

| Aqueous hair spray formulation | |
|---|---|
| | % by Wt |
| Water | to 100 |
| Ethanol DEB 100 | 30 |
| Natrasol (HEC) 2% solution | 5 |
| Active under test | qs (to provide 2.5% of active) |
| TEA | to pH 6.0 |

Study Procedure

1. Hair tresses were cut into swatches of 15 mm width and labelled A, B, C and D.
2. All swatches were welted by quick submersion in water then soaked in a 10% SLES solution for 30 seconds and finally rinsed with water.
3. All swatches were then dried in a straight configuration under ambient conditions.
4. Swatch A was treated with five pump sprays (0.9 g) of water and combed through to ensure an even coverage.
5. Swatch B was treated with five pump sprays (0.9 g) of the formulation without active under test and combed through to ensure an even coverage.
6. Swatch C was then treated with five pump sprays (0.9 g) of the formulation containing Preparation 1 and combed through to ensure an even coverage.
7. Swatch D was then treated with five pump sprays (0.9 g) of the formulation containing Gafquat 755N and combed through to ensure an even coverage.
8. All swatches were then left overnight in ambient conditions to dry.
9. The hair swatches were assessed using a blind test to rank the samples for appearance and feel as described below.

Panel Assessment Protocol

Seven people, both male and female and of differing ages, were used as the assessment panel. To minimise any bias the four hair swatches were each combed twice and laid out straight on a flat surface in a random order, prior to evaluation.

The panel were asked to look at the hair swatches and rank them 1 (best) to 4 (worst) on appearance and feel.

The results are expressed using the average of the ranks. The results have been statistically analysed using the Friedman's analysis of variance by ranks. A null hypothesis is applied which assumes that there is no differences between any of the hair samples and the mean ranks are due simply to chance. The analysis then determines if the null hypothesis should be retained or if it should be rejected. If the null hypothesis is rejected the analysis then will determine between which hair samples there are statistical differences.

Results—Appearance.

The results for hair swatch appearance assessment are given in table 2.

TABLE 2

| | Water | Formulation | Preparation 1 | Gafquat 755N |
|---|---|---|---|---|
| Mean rank | 3.7 | 2.3 | 1.3 | 2.7 |
| SD | 0.49 | 0.76 | 0.49 | 1.11 |
| Rank | 4 | 2 | 1 | 3 |

The statistical analysis concluded that the hair treated with the formulation containing Preparation 1 is significantly better in appearance than the swatches treated with Gafquat 755N or with water. (P<0.05) There was no significant difference between the formulation containing Preparation 1 and the formulation alone.

Results—Feel

The results for hair swatch feel assessment are given in table 3.

TABLE 3

|  | Water | Formulation | Preparation 1 | Gafquat 755N |
|---|---|---|---|---|
| Mean rank | 2.1 | 2.0 | 1.0 | 4.0 |
| SD | 0.69 | 0.82 | 1.07 | 0.00 |
| Rank | 3 | 2 | 1 | 4 |

Statistical analysis displayed that the hair swatch treated with the formulation containing Preparation 1 is significantly better than the swatch treated with Gafquat 755N (P<0.05). There is no significant statistical difference between the swatches treated with the formulation containing Preparation 1 and the formulation alone.

Example 3

Tack Test

Tack Test Protocol

The texture and feel of a product, when applied to a substrate such as hair, is an important factor in addition to its appearance and performance on hair. One important factor that impacts on the feel of a product is tack, or stickiness. Styling products are, by nature of their holding properties, susceptible to leaving a sticky feel on the hair or hands after application; this is undesirable. A fixative that can provide good hold without imparting stickiness to hair is desirable.

The method used for assessing the stickiness of the formulation is the tack test. This method is carried out on a Dia-Stron Mini Tensile Tester (MTT). The instrument composes of two flat metal disks connected vertically via a screw-threaded bar. The top plate has controlled movement up and down and can exert a specified amount of pressure onto the bottom plate.

Figure 2:
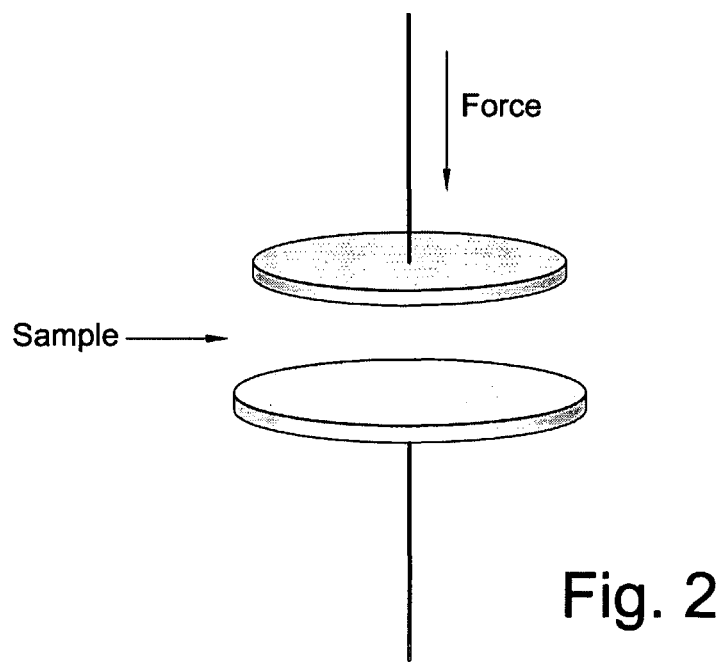
FIG. 2: Applying compression forces to test formulation in assessment of stickiness according to the Track Test.

The test formulation is placed on the centre of the lower plate. The upper plate then moves downwards compressing the test material and applying the required force (FIG. 2).

Figure 3:
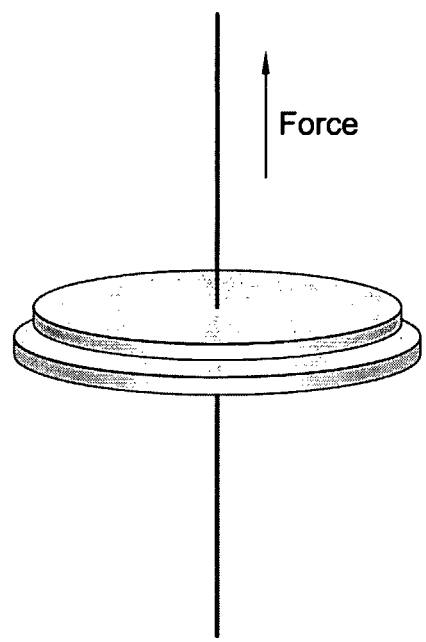
FIG. 3: Removing compression forces from test formulation in assessment of stickiness according to the Track Test.

The top plate then proceeds upwards removing the applied pressure (FIG. 3). As the plates begin to separate, the product or formulation under test will exert an opposing force trying to hold the two plates together. The magnitude of this opposing force is proportional to the tack of the product or formulation under test. A product or formulation that is stickier will produce a larger force opposing the separation of the plates.

Test Materials for Example 3
Hair spray formulation
Hair spray formulation with Preparation 1 (2.5% active).
Hair spray formulation with Gafquat 755 N (polyquaternium-11) (2.5% active)

|  | % by Wt |
|---|---|
| Aqueous hair spray | |
| Water | 65 |
| Ethanol DEB 100 | 30 |
| Natrasol (HEC) 2% solution | 5 |
| Active under test | qs (to provide 2.5% of active) |
| TEA | to pH 6.0 |

|  | % by Wt |
|---|---|
| MTT operating conditions | |
| Rate (mm/min) | 300 |
| Contact force (g) | 20 |
| Contact time (sec) | 2 |
| Cycles | 5 |
| Cycle repetitions | 5 |

All readings were taken under 50% RH and 25° C.

Protocol
1. 0.25 ml of the test solution was placed on the centre of the lower disk
2. Readings were taken using the parameters set out above
3. Five repetitions were carried out to yield a total of twenty five readings for each formulation Results The results for the tack testing are given in table 4.

TABLE 4

|  | Mean/gmf | SD | t | P |
|---|---|---|---|---|
| Preparation 1 | 296 | 61 | 42.3 | <0.0001 |
| Gafquat 755N | 441 | 120 | 31.8 | <0.0001 |
| Formulation | 224 | 107 | 18.1 | <0.0001 |

The tack has been reported as an average value as gmf (gram-force) at 50% RH 20-25° C. The tack of the formulation containing Preparation 1 was 296 gmf (p<0.001). This was lower than that for the formulation containing Gafquat 755N which had a value of 441 gmf (p<0.001). The tack of the formulation alone had a value of 224 gmf (p<0.001).

The inclusion of Gafquat 755N at 2.5% activity increased the tack of the formulation by 96% when compared to the control formulation without active. However the inclusion of Preparation 1 at 2.5% activity increased the tack of the formulation by only 32% when compared to the control formulation without active.

Example 4

Flyaway Assessment

Static flyaway is a common cosmetic condition, which is a result of an electrical charge build up on the hair surface. There are two primary factors involved in the generation of static charge on hair:
1. Interaction between hair and combs/brushes during grooming.
2. The difference in electrochemical potentials of the hair and comb's surfaces.

As a comb comes into contact with the hair equal and opposite charges are generated on the surface of the hair and the comb. This static charge consists of the generation of either ions or electrons on the surface of the hair. These charges repel causing each strand of hair to physically move away from every other charged strand. After separation of the comb from the hair, the dissipation of charge is governed by the electrical conductivity (electrical resistance) of the hair.

Increasing the electrical conductivity of the hair causing any static created to dissipate more rapidly can prevent static flyaway. Reducing the hair fibre friction will also inhibit the build up of the charge on the hair during combing.

The charge causes individual hair strands to physically push away from other strands. This creates the "ballooning or fan" effect. The measurement of this can be taken by measuring the angle in degrees to which the hair, tied at one end, fans out.

Materials for Example 4
Virgin European brown hair (De Meo)
10% Sodium laureth sulphate (SLES)
Hair spray formulation with Preparation 1 (2.5% active).
Hair spray formulation with Gafquat 755 N (polyquaternium-11) (2.5% active)

Aqueous hair spray formulation

| | % by weight |
|---|---|
| Water | up to 100 |
| Ethanol DEB 100 | 30 |
| Natrasol (HEC) 2% solution | 5 |
| Active under test | qs (to provide 2.5% of active) |
| TEA | to pH 6.0 |

Protocol
1. Hair tresses were cut into swatches of 15 mm width and labelled A, B and C.
2. All swatches were wetted by quick submersion in water then soaked in a 10% SLES solution for 30 seconds and finally rinsed in water.
3. All swatches were then dried in a straight configuration under ambient conditions.
4. Swatch A was then treated with five pump sprays (0.9 g) of water and combed through to ensure an even coverage.
5. Swatch B was then treated with five pump sprays (0.9 g) of the formulation containing Gafquat 755N and combed through to ensure an even coverage.
6. Swatch C was then treated with five pump sprays (0.9 g) of the formulation containing Preparation 1 and combed through to ensure an even coverage.
7. All swatches were then left overnight under ambient conditions to dry.
8. All swatches were then conditioned at 35% RH 20-25° C. for 90 minutes before being combed ten times in a controlled manner and the angle of flyaway was recorded.

Results

Figure 4:
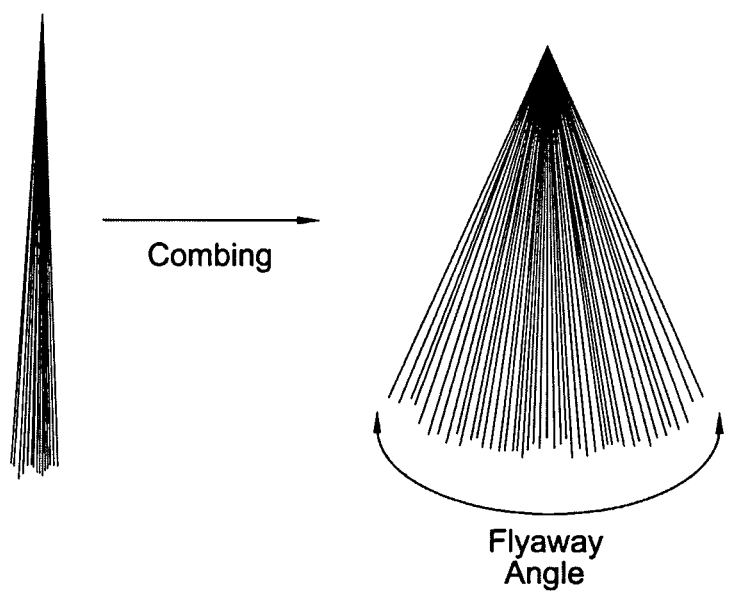
FIG. 4: Flyaway angle determined from combed hair according to the Flyaway Assessment.

The amount of flyaway is expressed as an angle as shown in FIG. 4. The results are shown in table 5.

TABLE 5

| | Water | Preparation 1 | Gafquat 755N |
|---|---|---|---|
| Mean angle | 103° | 57° | 87° |
| SD | 9.9 | 8.6 | 8.6 |
| t | 27.4 | 17.6 | 26.8 |
| p | <0.001 | <0.001 | <0.001 |

The results indicate that the hair tresses treated with formulation containing Preparation 1 displayed an average flyaway angle of 57° ($p<0.001$). The tress treated with the formulation containing Gafquat 755N displayed a flyaway angle of 87° ($p<0.001$) and the tress treated with water alone displayed a flyaway angle of 103° ($p<0.001$).

The formulations containing Gafquat 755N and Preparation 1 both showed a reduction in flyaway compared with the hair tress treated with water. The tress treated with the formulation containing Preparation 1 shows a 44% reduction in flyaway when compared against the tress treated with water. The hair tress treated with the formulation containing Gafquat 755N displays a 15% reduction in flyaway.

Curl Retention Studies

Example 5

Test Method

Purpose:
To evaluate the humidity resistance of curled hair treated with commercial hair fixatives.
Materials:
Materials used for the study are as following:
1. Mannequin with straight, fine, long brown hair (Mfd by Mariane, China)
2. Salon Care mannequin holder #292524 (Dist: Brentwood Beauty Labs International, Inc. P.O. Box 893, Hillside, Ill. 60162)
3. Starlite Comb #73—wide tooth (Mfg: DuPont)
4. Cleopatra #441 Professional rat tailed comb.
5. 1¾" Diane Professional Magnetic roller
6. 1½" Diane Professional Magnetic roller
7. 1" Diane Professional Magnetic roller
8. ¾" Diane Professional Magnetic roller
9. Temperature/Humidity Chamber, Model # PR-2FPH, Tabai Espec Corp., Osaka, Japan.
10. Sony Digital Camera
Formulations Used:
1. Low Cost Clear Shampoo, Croda, Inc. Proprietary Formulation SH-57-1
2. Test formulation with Mirustyle MFP
3. Test formulation with competitive fixative
Procedures:
In preparation for test product application,
1. The mannequin hair is washed using 2 oz of clear shampoo SH-57-1. Shampoo is distributed evenly through out the hair and wash for 2 minutes. Mannequin hair is then rinsed with warm tap water for 3 minutes to ensure removal of shampoo. The mannequin hair is towel dried and placed on the mannequin holder.
2. Forty (40) gm of test formulation is evenly distributed all over the hair. The mannequin hair is combed thoroughly using wide toothed comb to ensure that each strand of hair is evenly coated with the test product.
3. The hair is then sectioned into four portions. The first section is divided by using wide toothed comb and placing it at the center of the forehead and drawing it straight down to the center of back and middle of the neck and then from crown to ear on both right and left sides.
4. When each side is divided, a Cleopatra #441 Professional rat tailed comb is used to make 1" section of hair and roller is placed and held with aluminum hair clip.
5. Right and Left fronts of mannequin head are prepared as follows:
   a. Top of head: 1¾" Diane Professional Magnetic roller is placed
   b. Next section: 1½" Diane Professional Magnetic roller is placed
   c. Next section: 1" Diane Professional Magnetic roller is placed
   d. Next section: ¾" Diane Professional Magnetic roller is placed
6. Right and Left backs of mannequin head are prepared as follows:
   a. Top section: 1¾" Diane Professional Magnetic roller is placed
   b. Next section: 1¾" Diane Professional Magnetic roller is placed c. Next section: 1½" Diane Professional Magnetic roller is placed
d. Next section: 1½" Diane Professional Magnetic roller is placed
e. Next section: ¾" Diane Professional Magnetic roller is placed
7. The treated mannequin head is left to dry overnight at ambient temperature and humidity.
8. Next day the rollers are carefully removed so as not to disturb the curls.
9. The mannequin head is placed into the pre-conditioned Temperature and Humidity Chamber (Temp.=23° C.; RH=as required).
10. The mannequin is checked every ten minutes to observe the changes in the curls. The changes are documented using Sony Digital Camera.

| Styling Gel Formulation for Curl Retention Studies | |
| --- | --- |
| Part A | |
| Deionised Water | to 100% |
| Carbopol Ultrez 21 (thickener) | 1.00% |
| Triethanolamine | 1.00% |
| Part B | |
| Styling Polymer | 2.5% active |
| Hydrosolanum (conditioner) | 1.00% |
| Crovol PK-70 (plasticiser) | 1.00% |
| Germaben II (preservative) | 1.00% |

Viscosity = 86,000 cps, pH = 6.0

Figure 5:
FIG. 5: Evaluation of humidity resistance of treated curled hair.
Figure 6:
FIG. 6: Evaluation of humidity resistance of treated curled hair.
Figure 7:
FIG. 7: Evaluation of humidity resistance of treated curled hair.
Figure 8:
FIG. 8: Evaluation of humidity resistance of treated curled hair.

Results
1. Curl retention after 4 hours at 85% Relative Humidity—comparison of Preparation 1 and PVP. Styling gel formulation containing Preparation 1 demonstrates superior curl retention as shown in FIG. 5 when compared with FIG. 6.
2. Half head analysis of curl retention, initially and after 4 hours at 98% Relative Humidity—comparison of Preparation 1 and poly vinylpyrrolidone/vinyl acetate (PVP/VA) copolymer. Styling gel formulation containing Preparation 1 demonstrates superior curl retention as shown in FIG. 7 when compared with FIG. 8.

Example 6

Frizz Reduction

Materials
Pre tressed virgin European wavy brown hair
10% Sodium laureth sulphate (SLES)
Hair spray formulation
Hair spray formulation with Preparation 1

| Aqueous hair spray formulation | |
| --- | --- |
| | % by Wt |
| Water | 65 |
| Ethanol DEB 100 | 30 |
| Natrasol (HEC) 2% solution | 5 |
| TEA | to pH 6.0 |

Study Procedure
1. The tresses of hair were cut into swatches of 15 mm width and labelled A, B and C.
2. All swatches were wetted by quick submersion in water then soaked in a 10% SLES solution for 30 seconds and rinsed. Then allowed to dry.
3. Swatch A was then treated with five pump sprays (0.9 g) of water and combed through to ensure an even coverage.
4. Swatch B was then treated with five pump sprays (0.9 g) of the aqueous hair spray formulation and combed through to ensure an even coverage.
5. Swatch C was then treated with five pump sprays (0.9 g) of the aqueous hair spray formulation containing Preparation 1 and combed through to ensure an even coverage.
6. All swatches were then left overnight under ambient conditions to dry.
7. Once dry they were re-combed.
8. All swatches were then conditioned at 70% RH 20-25° C. for 120 minutes before being photographed.

Example 6

Results

Preparation 1 exhibits excellent anti-frizz functionality as can be seen when comparing FIG. 11 with FIGS. 9 and 10.

The invention claimed is:
1. A method of fixing hair, comprising fixing hair with a non-tacky hair fixative composition containing a cationically modified, hydrolysed starch;
   wherein:
   i) a native starch is hydrolysed to the extent of having a dextrose equivalent (DE) of about 2;
   ii) the hydrolysed starch is cationically modified, said cationic modification being carried out after hydrolysis; and
   iii) the non-tacky hair fixative composition has good hold and improved humidity resistance.
2. The method as claimed in claim 1, wherein the hydrolysed starch is cationically modified using a reagent containing a group selected from amino, imino, ammonium, sulfonium, or phosphonium groups.
3. The method as claimed in claim 1, wherein the hydrolysed starch is cationically modified using a reagent containing a tertiary amine or a quaternary amine group.
4. The method as claimed in claim 1, wherein the hydrolysed starch is cationically modified using a reagent selected from the group comprising 3-chloro-2-hydroxypropyltrimethylammonium chloride and epoxytrimethylammonium chloride.
5. The method as claimed in claim 1 wherein, said composition contains from 0.5 to 25% by weight of the cationically modified, hydrolysed starch.
6. The method as claimed in claim 1, wherein said composition contains 1% to 10% by weight of the cationically modified, hydrolysed starch.
7. The method of claim 1, wherein the native starch is obtained from a plant.
8. The method of claim 1, wherein the native starch is obtained from cereals, tubers, roots, legumes or fruits.
9. The method of claim 1, wherein the native starch is obtained from corn, pea, potato, sweet potato, banana, barley, wheat, rice, sago, amaranth, tapioca, arrowroot, canna, sorghum, or waxy or high amylose varieties thereof.

* * * * *